United States Patent [19]

Petersen et al.

[11] Patent Number: 5,354,760
[45] Date of Patent: Oct. 11, 1994

[54] CRYSTALLINE TIAGABINE MONOHYDRATE, ITS PREPARATION AND USE

[75] Inventors: Henning Petersen, Lyngby; Peter Nielsen, Herlev, both of Denmark; Michael Cain, Grayslake; Subhash Patel, Chicago, both of Ill.

[73] Assignee: Novo Nordisk A/S, Bagsvaerd, Denmark

[21] Appl. No.: 857,038

[22] Filed: Mar. 24, 1992

[30] Foreign Application Priority Data

Apr. 2, 1991 [DK] Denmark ............................. 0582/91

[51] Int. Cl.$^5$ ................. C07D 409/14; A61K 31/445
[52] U.S. Cl. ...................................... 514/326; 546/212
[58] Field of Search ........................ 546/212; 514/326

[56] References Cited

U.S. PATENT DOCUMENTS

| | | | |
|---|---|---|---|
| 4,721,723 | 1/1988 | Barnes et al. | 514/321 |
| 4,910,312 | 3/1990 | Pavia | 546/227 |
| 5,010,090 | 4/1991 | Gronvald et al. | 546/193 |

OTHER PUBLICATIONS

Pertwee et al., Neuropharmacology, vol. 27, No. 12, pp. 1265–1270 (1988).
Braestrup et al., Int. Congr. Ser.-Exerpta. Med. (Pharmacology), pp. 125–128 (1987).
Rustum et al., J. Chromatography, vol. 503, pp. 115–125 (1990).
Rekling et al., Br. J. Pharmacol. (1990), 99, pp. 103–106.

*Primary Examiner*—Marianne M. Cintins
*Assistant Examiner*—Phyllis G. Spivack
*Attorney, Agent, or Firm*—Steve T. Zelson; Cheryl H. Agris

[57] ABSTRACT

The invention provides crystalline Tiagabine hydrochloride monohydrate, process for its preparation, compositions containing the same and its therapeutic use as anti-epileptic agent.

11 Claims, 4 Drawing Sheets

CRYSTALLINE TIAGABINE MONOHYDRATE, ITS PREPARATION AND USE

This invention relates to crystalline Tiagabine and in particular to its monohydrate, its preparation and its use as a therapeutic agent.

Danish Patent no. 156398 discloses a class of novel compounds that exhibit gamma-aminobutyric acid-uptake (GABA-uptake) inhibitory properties and therefore said compounds are valuable for therapeutic use in the treatment of epilepsy and other CNS related diseases.

In Example 2 of Danish Patent 156398 the preparation of N-(4,4-di(3-methylthien-2-yl)-but-3-enyl)nipecotic acid hydrochloride is described.

In C. Braestrup et. al., Int. Congr. Ser.-Exerpta Med., 1987, 750 (Pharmacology), 125–8(Ref. 1)), various stereo-isomers of said compound are mentioned.

In Ref. (1) it is described that N- (4,4-di(3-methyl-thien2-yl)-but-3-enyl)nipecotic acid hydrochloride is available in its R-,S-, S- and R-form and that the R-isomer is the preferred form due to better inhibitory effect of $^3$H-GABA-uptake into rat forebrain synaptosomes.

In the present invention the R-isomer of N-(4,4-di(3-methylthien-2-yl)but-3-enyl-nipecotic acid is referred to by its generic name of Tiagabine (proposed INN).

In Danish Patent 156398 the preferred salts of N-(4,4-di(3-methylthien-2-yl)-but-3-enyl)nipecotic acid are described.

In example 2 of the same patent the most preferred salt of N-(4,4-di(3-methylthien-2-yl)-but-3-enyl)nipecotic acid is indicated to be the hydrochloride.

Further, it is described that the final crystallization of the hydrochloride salt takes place with ethyl acetate as the crystallizing solvent.

The method of preparation as described in the Danish Patent 156398 is applicable also for the crystallization of the preferred stereochemical form of the compound, the R-isomer. This method of preparation is rather labourous because purification by column chromatography has been be applied before a crystalline compound could be obtained. This kind of purification is rather expensive and unwanted in a commercial production process.

Furthermore analysis has shown that products manufactured by this process contain unwanted amounts of the crystallizing solvent, ethyl acetate.

Use of alternative organic solvents such as acetonitrile, butyl acetate, toluene, acetone, dichloromethane etc. also gives products containing various amounts of the used crystallizing solvent.

These solvents are unwanted because they are either toxic to humans or may give rise to interaction-reactions with other ingredients in the pharmaceuical preparation, resulting in low stability of the dosage form.

Further it has been found that the compound is heavily soluble in the applied organic solvents, which is very inconvenient when working on larger scale.

It has now been discovered that these disadvantages can be avoided by a new process giving crystals in a manner which is reproducible in a production scale.

The present invention provides R(−)N-4,4-di(3-methylthien-2-yl)-but-3-enyl nipecotic acid hydrochloride monohydrate crystals as a novel material, in particular in pharmaceutically acceptable form.

It has now been found that water can be used as a crystallizing solvent for this compound giving very reproducible results of a monohydrate crystal form. These products are stable under normal storage conditions and is very applicable for the pharmaceutical formulations as the only residual solvent in the product is water.

Tiagabine hydrochloride as monohydrate crystals is stable and non-hygroscopic. It is characterized by an X-ray powder diffractogram as shown in FIG. 1. A typical $^1$H-NMR spectrum is shown in FIG. 2 and a typical IR-spectrum of the crystals in KBr is shown in FIG. 3. The DSC profile of the monohydrate is shown in FIG. 4.

Under desiccation conditions the bound water may partly be removed, but on exposure to normal humidity the crystals very rapidly will take up water to reform the monohydrate.

The present invention also provides a process for producing crystalline Tiagabine hydrochloride monohydrate, which comprises crystallizing Tiagabine hydrochloride monohydrate from an aqueous solution containing from one to several equivalents of hydrogen chloride. The solution may be obtained either by dissolving the compound as the amphoteric salt or by dissolving the hydrochloride of the compound. Hydrochloric acid can be added either as a diluted or as a concentrated solution in the range of 1–10 equivalents to the aqueous solution of Tiagabine.

The aqueous solution of Tiagabine is usually made at temperatures ranging from 40° –75° C. Higher temperatures may be used, but is not necessary as yields are very high using the above mentioned range. The solution may be seeded in order to start the crystallization, but this can also be omitted.

The aqueous solution of Tiagabine can further be obtained by acid catalyzed hydrolysis of R(−)-ethyl-N-(4,4-di(3-methylthien-2-yl)-but-3-enyl)nipecotate in aqueous solution. The acid catalyzed hydrolysis can be carried out by using e.g. phosphoric acid, sulfuric acid, hydrobromic acid, hydrochloric acid or hydroiodic acid, preferably hydrochloric acid.

The crystals can be isolated from the solution by normally used procedures, such as filtration, centrifugation etc. The crystals can be rinsed by pure water or a diluted hydrochloric acid solution before drying. Drying can be performed either under vacuum or at normal pressure.

The present invention also provides a pharmaceutical composition comprising crystalline Tiagabine monohydrate which comprises crystalline tiagabine monohydrate and a pharmaceutically acceptable carrier.

The compositions of this invention are usually adapted for oral administration, but formulations for dissolution for parenteral administration are also within the scope of this invention.

The composition is usually presented as a unit dose composition containing from 1 to 200 mg, more usually from 2 to 100 mg, for example 2 to 50 mg such as 2, 4, 8, 10, 20, 25 or 30 mg. Such composition is normally taken from 1 to 6 times daily, for example 2, 3 or 4 times daily so that the total amount of active agent administered is within the range 4 to 400 mg.

Preferred unit dosage forms include tablets or capsules.

The composition of this invention may be formulated by conventional methods of admixture such as blending, filling and compressing.

Suitable carriers for use in this invention include a diluent, a binder, a disintegrant, a colouring agent, a flavouring agent and/or a preservative. These agents may be utilized in conventional manner, for example in a manner similar to that already used for clinically used epileptic agents.

The invention also provides a method of treatment of epilepsy in mammals including humans which method comprises administering an effective amount of pharmaceutically acceptable crystalline Tiagabine monohydrare.

The invention further provides pharmaceutically acceptable crystalline Tiagabine hydrochloride monohydrate for use in the treatment of epilepsy.

EXAMPLE 1

Figure 1:
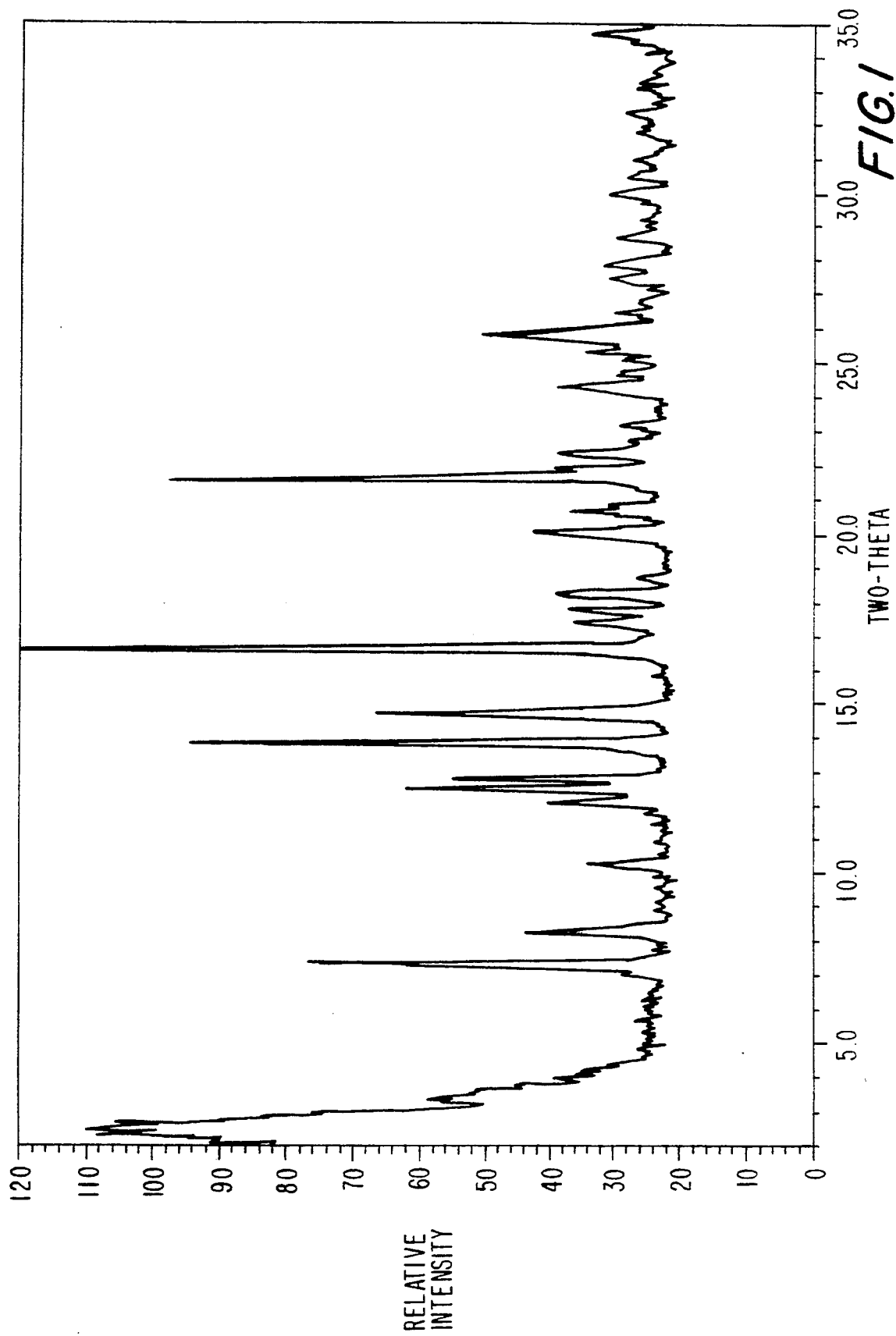
FIG. 1 shows X-Ray powder diffractogram, Tiagabine hydrochloride monohydrate.
Figures 2A, 2B:
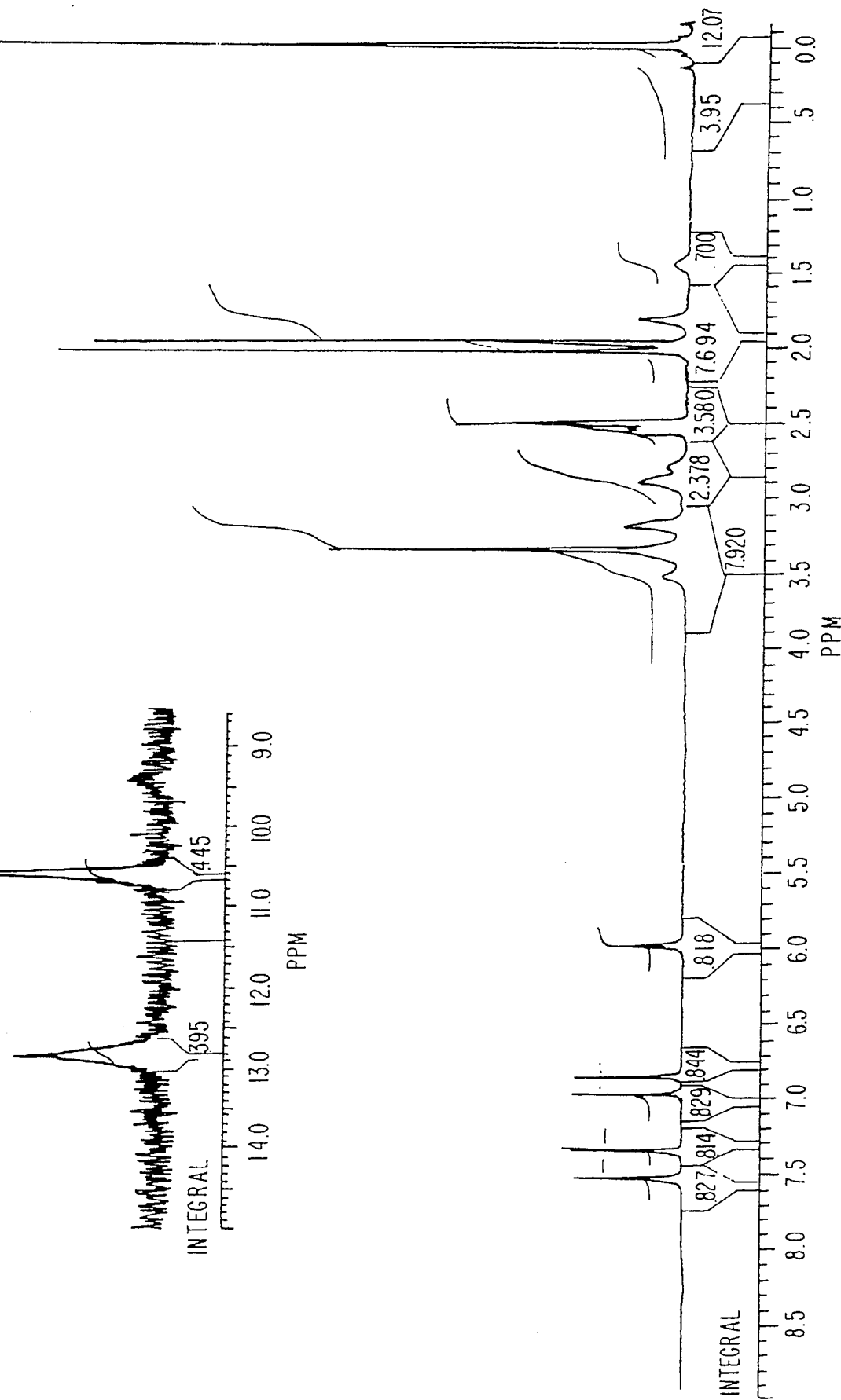
FIG. 2 shows $^1$H-NMR-spectrum, Tiagabine hydrochloride monohydrate.

A. Crude
R(−)-N-(4,4-di(3-methylthien-2-yl)-but-3-enyl nipecotic acid, hydrochloride 1.200 g of R(−)-Ethyl-N-(4,4-di(3-methylthien-2-yl)-but-3-entyl)nipecotate was dissolved in 12 l of 90% ethanol. 360 ml of 36% aqueous solution of sodium hydroxide was added at room temperature. 10 l of water was added slowly under good stirring. When all starting materials had been hydrolized, pH was adjusted to 4.5 with dilute hydrochloric acid. The ethanol was stripped off. The product precipitated as an oil in the water. The oil was taken up in dichloromethane and the water phase was discarded. The organic phase was dried and 0.9 equivalent of dry HCl was added to the solution at 15° C. After stirring overnight the product was recovered by filtration and dried in vacuo at 40° C. Yield: 1170 g of crude crystalline material.

B. Crystallization of
R(−)-N-(4,4-di(3-methylthien-2-yl)-but-3-enyl)nipecotic acid, hydrochloride monohydrate 1.050 g of crude product was dissolved in 6000 ml of water at 60° C. The solution was filtered to remove any undissolved matter. 1400 g of 1N aqueous hydrochloric acid was added at 60° C. At 45° C. the solution was seeded. After 2 h the temperature was lowered to 10° C. The crystalline product was recovered by filtration and dried in vacuo at 40° C. Yield: 960 g.

DSC onsett: 82.6° C.
$^1$H-NMR: comply
HPLC purity: 99.4
X-Ray: comply
H$_2$O: 4.6%

EXAMPLE 2

R(−)-N-(4 4-di(3-methylthien-2-yl)-but-3-enyl)nipecotic acid, hydrochloride monohydrate 220 g of crude R(−)-N-(4,4-di(3-methylthien-2-yl)-but-3-enyl)nipecotic acid, hydrochloride was dissolved at 50° C. in 1100 ml of water. At 40° C. the solution was seeded and crystallisation started giving a suspension of fine crystals. The suspension was cooled to 0° C. before filtration. The filtercake was washed with cold water before drying in vacuo at 60° C. Yield: 193 g.

HPLC purity: 99.3%

EXAMPLE 3

R(−)-N-(4 4-di(3-methylthien-2-yl)-but-3-enyl)nipecotic acid, hydrochloride monohydrate Dissolve 174 g of crude product in 5200 ml of water at 40–50° C. Add 145 ml of conc. hydrochloric acid (37%) to the solution under good stirring. At 40° C. 0.5 g of seed crystals are added. The mixture is stirred for 4 h at 40° C. before cooling to 20° C. The solid is filtered and vacuum dried at 40° C. overnight. Yield: 140 g.

HPLC purity: 99.7%

The reproducibility is further illustrated by the following results (Table 1) where batches (A–G) are crystallized using different concentrations of the compound and of HCl:

TABLE 1

REPRODUCIBILITY OF CRYSTALLISATION FROM WATER OF [R(-)-N-(4,4-di(3-methylthien-2-yl)-but-3-enyl)nipecotic acid, hydrochloride, monohydrate]

| Batch | RECRYSTALLIZATION CONDITIONS | | | | DRYING CONDITIONS | | YIELD % | H$_2$O % | DSC Onset/max | Purity HPLC % | X-Ray |
|---|---|---|---|---|---|---|---|---|---|---|---|
| | eqv.HCL added | Dissolv. °C. | Conc. g/l | Filter °C. | Temp. °C. | Time h | | | | | |
| A | 0 | 60 | 200 | 5 | 45 | 16 | 70 | 4.9 | 81.6/84.6 | 99.6 | comply |
| B | 0.5 | 60 | 130 | 5 | 45 | 16 | 86 | 4.9 | 81.6/83.6 | 99.5 | comply |
| C | 4.4 | 40 | 32 | 10 | 45 | 16 | 86 | 4.0 | 81.8/84.0 | 99.6 | comply |
| D | 0.5 | 60 | 100 | 8 | 50 | 16 | 96 | | 82.2/83.6 | 99.2 | comply |
| E | 0.5 | 60 | 100 | 5 | 40 | 64 | 95 | 4.9 | 80.8/85.4 | 99.5 | comply |
| F | 0 | 60 | 200 | 5 | 40 | 16 | 91 | 4.7 | 81.1/85.9 | 98.0 | comply |
| G | 0.5 | 60 | 100 | 5 | 40 | 16 | 95 | 4.8 | 83.0/84.6 | 99.3 | comply |

EXAMPLE 4

R(−)-N-(4,4-di(3-methylthien-2-yl)-but-3-enyl)nipecotic acid, hydrochloride monohydrate 26 g of R(−)-ethyl-N-(4,4-di(3-methylthien-2-yl)-but-3-enyl)nipecotate, hydrochloride is dissolved in 385 ml of water. Under good stirring is added 5 ml of conc. hydrochloric acid and the solution is heated to reflux for 5–10 hours until the reaction is completed. The solution is concentrated by distilling off 30–50% of the solvent. Extract with 40 ml of toluene. To the aqueous layer is added hydrochloric acid and the solution is cooled to 5° C. before the product is filtered off and dried in vacuo at 40° C. Yield: 20 g of R(−)-N-(4,4-di(3-methylthien-2-yl)-but-3-enyl)nipecotic acid, hydrochloride monohydrate.

HPLC purity: 99.5%
X-Ray: comply

H₂O: 4,6%

We claim:

1. Crystalline R(−)-N-(4,4-di(3-methylthien-2-yl)-but-3-enyl)nipecotic acid hydrochloride monohydrate having a differential scanning calorimetry profile with an onset from about 80.8° C. to about 83.0° C.

Figure 3:
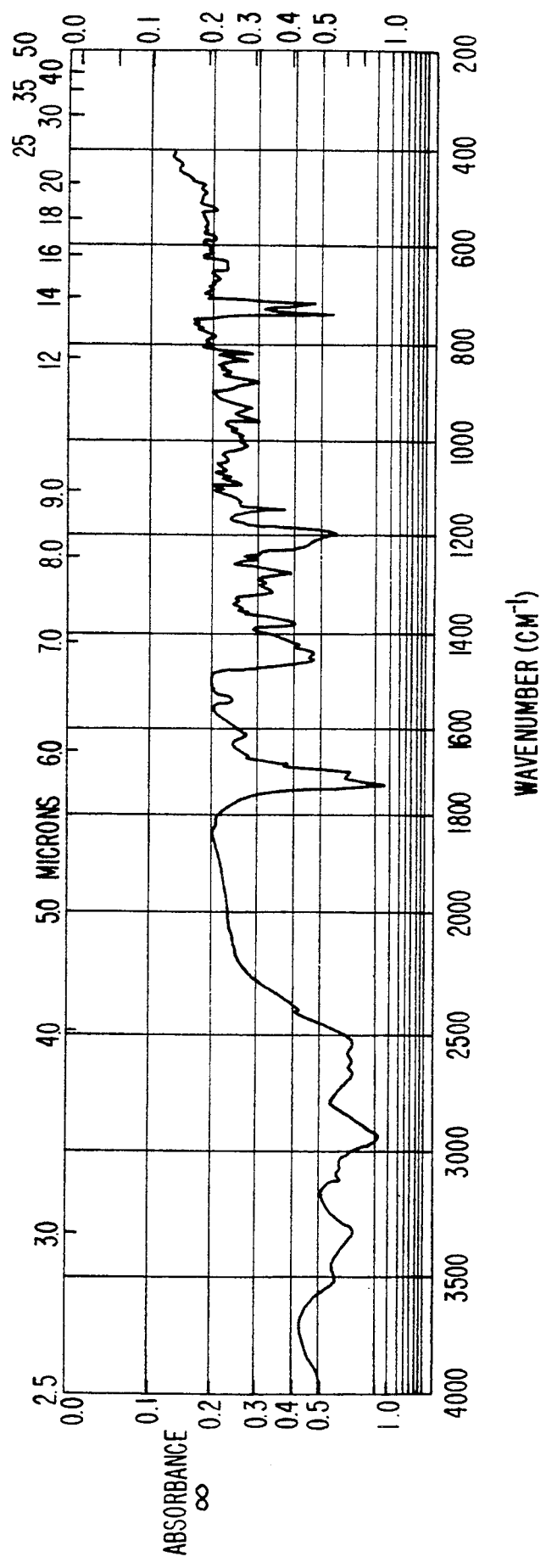
FIG. 3 shows Infra-Red-spectrum of Tiagabine hydrochloride monohydrate crystals in KBr.
Figure 4:
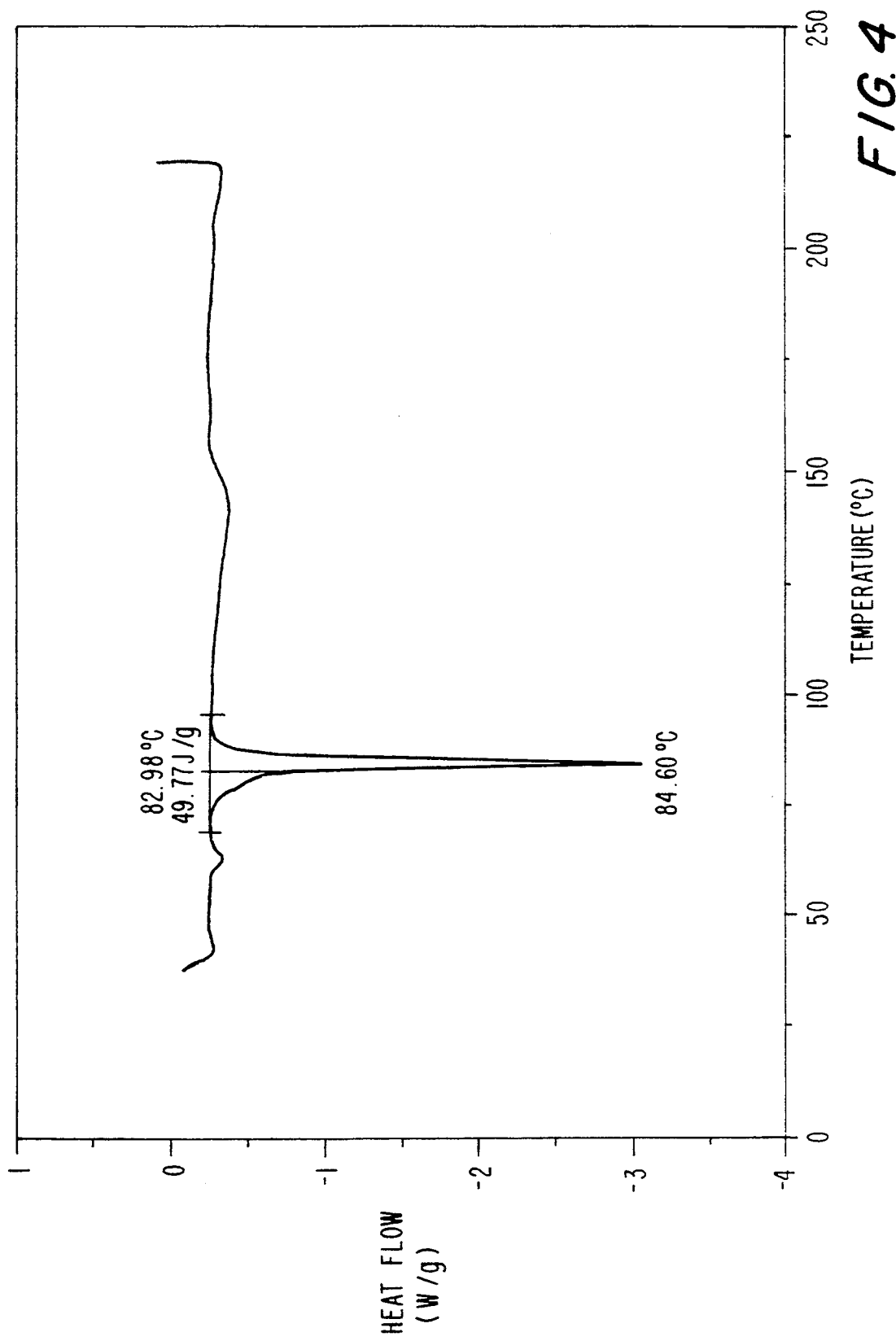
FIG. 4 shows DSC profile of Tiagabine hydrochloride monohydrate.

2. Crystalline R(−)-N-(4,4-di(3-methylthien-2-yl)-but-3-enyl)nipecotic acid hydrochloride monohydrate, having substantially the same X-ray diffractogram as set out in FIG. 1 and substantially the same IR spectrum, in KBr, as set out in FIG. 3.

3. A process for the preparation of crystalline R(−)-N-(4,4-di(3-methylthien-2-yl)-but-3enyl)nipecotic acid hydrochloride monohydrate, which process comprises forming an aqueous solution of R(−)-N-(4,4-di(3-methylthien-2-yl)-but-3-enyl)nipecotic acid hydrochloride and crystallizing said R(−)-N-(4,4-di(3-methylthien-2-yl)-but-3-enyl)nipecotic acid hydrochloride monohydrate from solution by precipitation or recrystallization from water.

4. A process for the preparation of crystalline R(−)-N-(4,4-di(3-methylthien-2-yl)-but-3-enyl)nipecotic acid hydrochloride monohydrate comprising acid catalyzed hydrolysis of the ethyl ester of R(−)-N-(4,4-di(3-methylthien-2-yl)-but-3-enyl)nipecotic acid hydrochloride in an aqueous solution followed by crystallization of R(−)-N-(4,4-di(3-methylthien-2-yl)-but-3-enyl)nipecotic acid hydrochloride monohydrate from the aqueous solution by precipitation or recrystallization from water.

5. A pharmaceutical composition comprising an effective anti-epileptic amount of crystalline R(−)-N-(4,4-di(3-methylthien-2-yl)-but-3-enyl)nipecotic acid hydrochloride monohydrate having a differential scanning calorimetry profile with an onset from about 80.8° C. to about 83.0° C. together with a pharmaceutically acceptable carrier or diluent.

6. The pharmaceutical composition according to claim 5 in the form of an oral dosage unit containing from 1 to 200 mg of R(−)-N-(4,4-di(3-methylthien-2-yl)-but-3-enyl)nipecotic acid hydrochloride monohydrate having a differential scanning calorimetry profile with an onset from about 80.8° C. to about 83.0° C.

7. A pharmaceutical composition comprising an effective anti-epileptic amount of crystalline R(−)-N-(4,4-di(3-methylthien-2-yl)-but-3-enyl)nipecotic acid hydrochloride monohydrate having substantially the same X-ray diffractogram as set out in FIG. 1 and substantially the same IR spectrum, in KBr, as set out in FIG. 3 together with a pharmaceutically acceptable carrier or diluent.

8. A method of treating epilepsy in a mammal comprising administering to the mammal an effective amount of crystalline R(−)-N-(4,4-di(3-methylthien-2-yl)-but-3-enyl)nipecotic acid hydrochloride monohydrate having a differential scanning calorimetry profile with an onset from about 80.8° C. to about 83.0° C.

9. A method of treating epilepsy in a mammal comprising administering to the mammal a pharmaceutical composition comprising an effective anti-epileptic amount of crystalline R(−)-N-(4,4-di(3-methylthien-2-yl)-but-3-enyl)nipecotic acid hydrochloride monohydrate having a differential scanning calorimetry profile with an onset from about 80.8° C. to about 83.0° C. together with a pharmaceutically acceptable carrier or diluent.

10. A method of treating epilepsy in a mammal comprising administering to the mammal an effective amount of crystalline R(−)-N-(4,4-di(3-methylthien-2-yl)-but-3-enyl)nipecotic acid hydrochloride monohydrate having substantially the same X-ray diffractogram as set out in FIG. 1 and substantially the same IR spectrum, in KBr, as set out in FIG. 3.

11. A method of treating epilepsy in a mammal comprising administering to the mammal a pharmaceutical composition comprising an effective anti-epileptic amount of crystalline R(−)-N-(4,4-di(3-methylthien-2-yl)-but-3-enyl)nipecotic acid hydrochloride monohydrate having substantially the same X-ray diffractogram as set out in FIG. 1 and substantially the same IR spectrum, in KBr, as set out in FIG. 3 together with a pharmaceutically acceptable carrier or diluent.

* * * * *